United States Patent
Griss et al.

(10) Patent No.: US 8,087,141 B2
(45) Date of Patent: Jan. 3, 2012

(54) METHOD FOR PRODUCING A PRICKING ELEMENT

(75) Inventors: Patrick Griss, Otelfingen (CH);
Marzellinus Zipfel, Freiburg (DE);
Angel Lopez, Pforzheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1175 days.

(21) Appl. No.: 11/763,266

(22) Filed: Jun. 14, 2007

(65) Prior Publication Data

US 2008/0040919 A1   Feb. 21, 2008

Related U.S. Application Data

(63) Continuation of application No. PCT/EP2005/013266, filed on Dec. 10, 2005.

(30) Foreign Application Priority Data

Dec. 17, 2004   (EP) ..................................... 04029926

(51) Int. Cl.
*B21D 53/00*   (2006.01)
(52) U.S. Cl. ............................... 29/424; 29/557; 216/41
(58) Field of Classification Search .................... 29/424, 29/458, 557; 216/2, 41; 600/576; 604/272
See application file for complete search history.

(56) References Cited

U.S. PATENT DOCUMENTS

| | | | |
|---|---|---|---|
| 4,777,096 A | 10/1988 | Borysko | |
| 5,476,575 A * | 12/1995 | Brophy et al. | 205/652 |
| 5,855,801 A | 1/1999 | Lin et al. | |
| 6,406,638 B1 | 6/2002 | Stoeber et al. | |
| 6,610,235 B1 | 8/2003 | Lebouitz et al. | |
| 6,815,360 B1 | 11/2004 | Canham et al. | |
| 2002/0193754 A1 | 12/2002 | Cho | |
| 2003/0171699 A1 * | 9/2003 | Brenneman | 600/584 |
| 2003/0212347 A1 | 11/2003 | Sohrab | |
| 2006/0086689 A1 * | 4/2006 | Raju | 216/2 |

FOREIGN PATENT DOCUMENTS

| | | |
|---|---|---|
| EP | 0 445 820 | 9/1991 |
| EP | 1 346 686 | 9/2003 |
| WO | WO 02/077638 | 10/2002 |
| WO | WO 2004/008203 | 1/2004 |

OTHER PUBLICATIONS

Lebouitz, et al., Microneedles and Microlancets Fabricated Using Soi Wafers and Isotropic Etching, Department of Mechanical Engineering and Berkeley Sensor and Actuator Center, Berkeley, CA.

(Continued)

*Primary Examiner* — Jermie Cozart
(74) *Attorney, Agent, or Firm* — Bose McKinney & Evans LLP

(57) ABSTRACT

The sheet metal or substrate material 22 is constructed by a photo-chemical machining or milling method. In this exemplary process, an etching mask 24 is applied to both sides of the substrate 22 and covers the structure of the flat-shaped member 12, which is to be uncovered in a subsequent etching step. The mask 24 is formed by coating the substrate 22 with a photoresist and is exposed through a photomask having the desired pattern that is arranged in front of the mask, whereby the photoresist is polymerized or hardened in the covered areas while the other areas are rinsed away after development.

24 Claims, 4 Drawing Sheets

OTHER PUBLICATIONS

Brazzle, John et al., Micromachined Needle Arrays for Drug Delivery or Fluid Extraction, IEEE Engineering in Medicine and Biology, Nov. 1999, pp. 53-58.

Stupar, Philip et al., Silicon, Parylene, and Silicon/Parylene Micro-Needles for Strength and Toughness, The 11th International Conference on Solid-State Sensors and Actuators, Jun. 2001.

McCallister, Devin et al., Microfabricated Microneedles for Gene and Drug Delivery, Annu. Rev. Biomed. Eng. 2000, pp. 289-313.

Smart, Wilson et al., The Use of Silicon Microfabrication Technology in Painless Blood Glucose Monitoring, Diabetes Technology & Therapeutics, vol. 2, No. 4, 2000, pp. 549-559.

Chen, Jingkuang et al., A Multichannel Neural Probe for Selective Chemical Delivery at the Cellular Level, IEEE Transactions on Biomedical Engineering, vol. 44, No. 8, Aug. 1997, pp. 760-769.

* cited by examiner

METHOD FOR PRODUCING A PRICKING ELEMENT

RELATED APPLICATIONS

This is a continuation application of International Application PCT/EP2005/013266, filed Dec. 10, 2005, which claims priority to EP 04029926.5, filed Dec. 17, 2004, which are hereby incorporated by reference in their entirety.

BACKGROUND

The present invention relates to a process for producing a lancing element for withdrawing bodily fluid in which a flat-shaped member is formed from a flat material by applying a mask and allowing an etching agent to act upon it. At least a part of the flat-shaped member is shaped as a tip for piercing into a body part of a test subject.

Lancing elements of this type are used for the analysis of very small amounts of fluid, especially in bioanalytics, such as those which are withdrawn in situ as capillary blood for blood glucose determinations. Such microfluidic systems, in addition to the microscopic volumes (microliters and less), are also characterized by structural elements of increasingly smaller dimensions which use capillary forces and can be implemented in so-called disposables in a suitable manner for mass production. Although manufacturing processes, especially in the form of mask etching (photochemical etching), are known from the field of semiconductor technology for highly-integrated systems, the materials used cannot generally be used for mechanically stressed structures due to their brittleness. When biocompatible materials such as steel are etched, a problem arises with conventionally shaped-complementary etch masking in which the generated lancing structures are rounded off at the tip and thus do not provide a particularly optimal puncture.

An etching process for producing surgical needles is known from U.S. Pat. No. 4,777,096, in which the etch mask extends beyond the tip to be formed in a distally blunted shaping area and is constructed to prevent rounding of the tip. However, this mask overhang is shorter than the undercutting width of the etching agent so that the tip is shaped by a combined lateral and frontal etching action which only slightly reduces the problem of blunting.

SUMMARY OF THE INVENTION

Embodiments incorporating the present invention address the disadvantages of the prior art and improve upon a production process of the type described above such that sharp lancing structures for optimal lancing into a body part are created in a process suitable for mass production without requiring complicated post-processing steps.

An exemplary embodiment produces a sharp tip solely by lateral and mutually converging etching agent fronts. In this embodiment, a mask is provided with a shaping area for the tip to be formed and a screening area which extends beyond this shaping area to prevent the tip from being etched off at the front. A sharp tip is exposed by laterally undercutting the side flanks or edges of the shaping and screening area. This can prevent the contour near the tip from being rounded off, whereby the etching process is terminated as soon as the bridge of material located between the side flanks of the etching mask is broken through. This allows optimized tips to be created in order to reduce the lancing pain and enable bodily fluid to be extracted with the smallest possible volume. Moreover, the required propulsion forces for lancing can be minimized and traumatization of the body tissue can be substantially reduced.

The shaping area advantageously narrows toward the screening area to produce a lancing shaft that tapers toward the tip. It is additionally advantageous when the shaping area is linearly chamfered at least on one side.

Another exemplary embodiment provides that at least one side flank is bent or concavely curved in the junction between the shaping area and screening area so that the substrate material in the area around the tip only has to be removed from the side.

In an embodiment, the mask is constructed such that the screening area has a constant or increasing width over a given screening length where it connects with the shaping area. The screening length should be larger than the proximal undercutting width due to the action of the etching agent. This prevents the tip from being centrally etched off.

The tip is formed as a result of a constriction in the mask where the width of the constriction is less than twice the lateral undercutting width so that the substrate material under the constriction is completely etched away.

The screening area is advantageously widened again after the constriction. To improve the stability of the etching mask, it is advantageous when the screening area has a widening bridge section distal to the tip.

While etching processes in steel mainly proceed isotropically, it is also conceivable that the lateral undercutting width is larger or smaller than the etching depth. Anisotropy, for example, occurs when the etching agent is applied at an overpressure relative to the surroundings in order to ensure a particularly effective etching action. The etching agent can be applied in a dipping bath or by being sprayed onto the flat material.

For high throughput, it is advantageous when the flat material that is formed from stainless steel sheet metal is processed from roll to roll by photo-chemical mask etching. However, it is also possible to use a semiconductor wafer as a flat material.

The thickness of the flat material is generally between 0.01 mm and 1 mm.

According to one exemplary embodiment, the lancing element is provided with a semi-open capillary channel to transport the bodily fluid, whereby the capillary channel is formed by a channel slot in the mask where the distal ends of the channel walls form a sharp tip. In this embodiment, the screening areas for the tips of the channel walls are delimited on one side by the channel slot.

In an embodiment of the shaped member, the flat material is covered on both sides with a mask, wherein a pointed lancing shaft is etched free on one side and a semi-open capillary channel with pointed channel walls that extend towards the lancing shaft is etched free on the other side.

According to another embodiment, the etching mask is provided with a compensation opening at a lateral distance from an undercut edge section and an edge contour of the flat-shaped member is etched away from the edge through a compensation opening under the action of the etching agent. Therefore, undesired undercuts on the shaped member are chemically milled off without additional manufacturing effort.

In order to remove the edges, it is advantageous when the compensation opening is a slot or chain of holes in the mask along the edge section. The compensation opening should have a smaller inner width than a cut-away or opening in the mask bordering the edge section.

In order to achieve a combined undercutting effect on a bridge of material extending between the edge of the mask and the compensation cut-out, the width of the overlying mask bridge should be less than the undercutting width of the etching agent measured from the edge of the mask.

Depending on the desired shape of the contour, an exemplary embodiment provides that the compensation opening is arranged in a shaping area and optionally in a screening area of the mask for the tip to be formed. In particular, it is advantageous when the compensation opening is laterally spaced apart from a bent or concavely curved side flank of the mask. The side flank is configured to be bent or concavely curved in a distal direction relative to the tip to be formed. The distal direction, or lancing direction, is the direction in which the lancing element moves to create a puncture.

In order to protect the tip from being etched away at the front, it is advantageous when the compensation opening is introduced at the side of a central axis running towards the tip that is to be formed so that a strip of the mask is retained in front of the tip along the central axis and at least beyond the undercutting width. In principle, the same considerations apply here with regard to avoiding a frontal action of the etching agent as already set forth with regard to the edge of the mask. In any case, a V-shaped contour of the compensation opening should be avoided.

BRIEF DESCRIPTION OF THE DRAWINGS

The above-mentioned embodiments of the present invention and the manner of obtaining them will become more apparent and the invention itself will be better understood by reference to the following description of the embodiments of the invention, taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
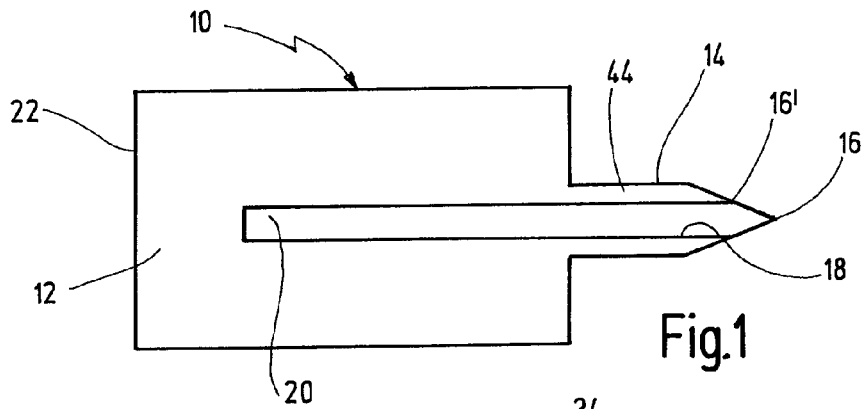
FIG. 1 is a top view of a lancing element with a tip and capillary channel for withdrawing blood.

The lancing and sampling element 10 shown in FIG. 1 is used as a disposable article to withdraw and transport a small amount of blood through capillary action from a body part of a test subject to an analytical site 20, for example, to carry out blood glucose measurements. In this exemplary embodiment, the lancing element 10 comprises a flat-shaped member 12, a lancing member 14 extending therefrom and having a tip 16, and a semi-open capillary channel 18 for blood transport through capillary action from the tip 16 to the analytical site 20.

The flat-shaped member 12 is made of a stainless steel metal sheet 22 having a thickness of about 100 to 300 μm. The member 12 has a proximal end section that forms a holding area for handling the lancing element 10 during the lancing process, whereas the lancing member 14, which is shaped as one piece at the distal end of the lancet element 10, generates a small cut in the skin of the user in order to remove microscopic volumes of blood. In this embodiment, the capillary channel 18 has a groove or is semi-open over its length so that it can be produced by photolithography. The withdrawn blood sample can be analyzed by reflection spectroscopic or electrochemical detection methods known in the art.

The sheet metal or substrate material 32 is constructed by a photo-chemical machining or milling method. In this exemplary process, an etching mask 24 is applied to both sides of the substrate 22 and covers the structure of the flat-shaped member 12, which is to be uncovered in a subsequent etching step. The mask 24 is formed by coating the substrate 22 with a photoresist and is exposed through a photomask having the desired pattern that is arranged in front of the mask, whereby the photoresist is polymerized or hardened in the covered areas while the other areas are rinsed away after development.

An etching agent is subsequently applied to the substrate 22 over the (double-sided) etching mask 24 so that the masked areas are etched away according to the basic shape of the mask 24. In an embodiment incorporating isotropic etching action, the depth of the removed material corresponds to the lateral etching rate for the undercutting of edge contours of the mask 24. The etching process can also take place anisotropically due to external influencing parameters or material properties of the substrate 22 where, for example, the lateral undercutting rate is larger or smaller than the depth etching rate.

Figure 10:
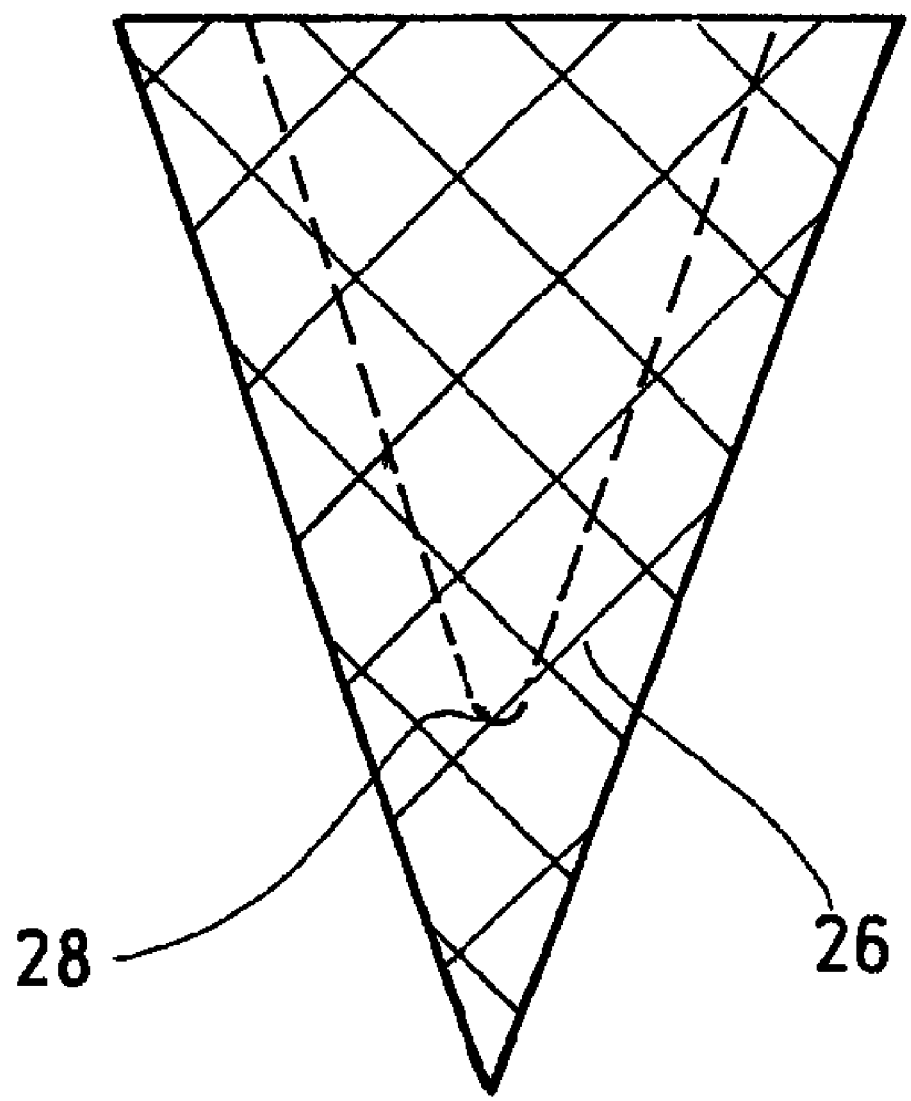
FIG. 10 shows a top view of an etching mask for producing a tip according to the prior art.

Manufacturing the tip 16 is particularly critical for the function of the lancing element 10. According to FIG. 10, an obvious approach according to the prior art would be to provide an etching mask with a pointed or triangular shaping area 26 corresponding to the desired contour of the finished part. However, the tip 28 formed in this manner is not sharp, but rather is rounded off due to the etching agent that flows in from all sides during undercutting of the triangular mask 26.

Figure 2:
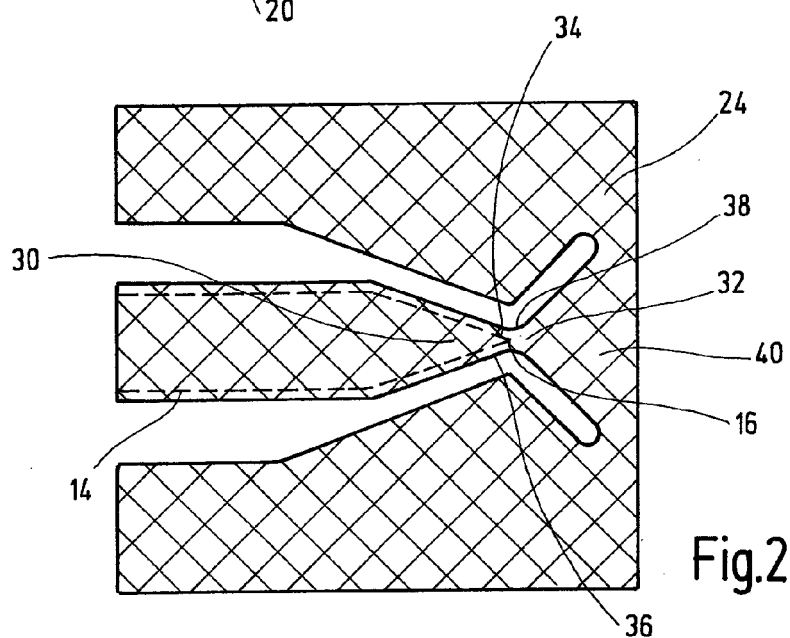
FIG. 2 is a top view of an etching mask for producing the tip of a lancing element.

In order to address the disadvantages of the prior art, an exemplary embodiment shown in FIG. 2 includes an etching mask 24 having a shaping area 30 for the tip 16 to be formed and an adjoining screening area 32 for preventing the front of the tip 16 from being etched off. The screening area 32 is distal with regard to the lancing direction, i.e., is positioned at or beyond tip 16 in the lancing direction. Similarly, the lancing direction of the mask 24 is the same direction in which the tip 16 to be formed points. The shaping area 30 narrows towards the screening area 32 and the side flanks or edges 34, 36 of the mask 24 are bevelled with a linear slope. Starting from the constriction 38, the screening area 32 widens while forming a bridge section 40 towards the other areas of the mask so that the etching mask 24 remains more stable.

Thus, a sharp tip 16 is etched free by lateral undercutting of the side flanks 34, 36 of the shaping area and screening area 30, 32, the contour of which is shown by the dashed line in FIG. 2. In this embodiment, the screening area 32 has a larger screening length than the undercutting width viewed in the proximal direction, whereas the width of the constriction 38 is less than twice the lateral undercutting width. Additionally, the etched away material fronts converge at the constriction 38 until the tip 16 is finally uncovered at the completion of the etching process.

Figure 3:
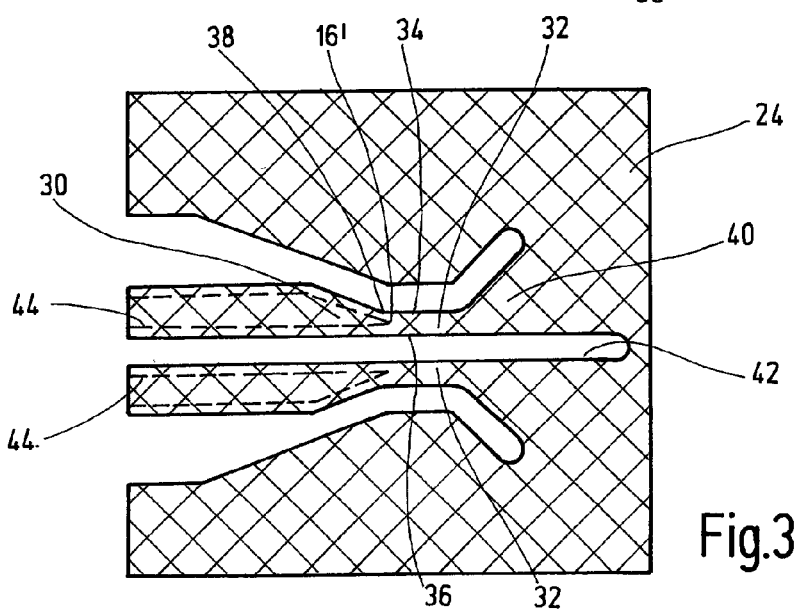
FIG. 3 is a top view of an etching mask for producing a capillary channel in the area of the tip of a lancing element.

The front face of the mask 24 shown in FIG. 3 is designed to provide the desired capillary channel 18 in the area of the lancing member 14. Accordingly, the mask 24 has a capillary slot 42 through which the channel 18 is etched to form the channel walls 44. In order to also facilitate lancing in this case, the distal ends of the channel walls 44 are chamfered as sharp tips 16'. This is achieved similar to the embodiments described above by providing screening areas 32 positioned at the distal end. In contrast to FIG. 2, the side flanks 34, 36 in the area of the constriction 38 are not concavely curved on both sides, but rather are bluntly angled on one side and linearly delimited on the opposite side by the capillary slot 42 to form a wedge-shaped tip 16' as shown by the dashed line.

Figure 4:
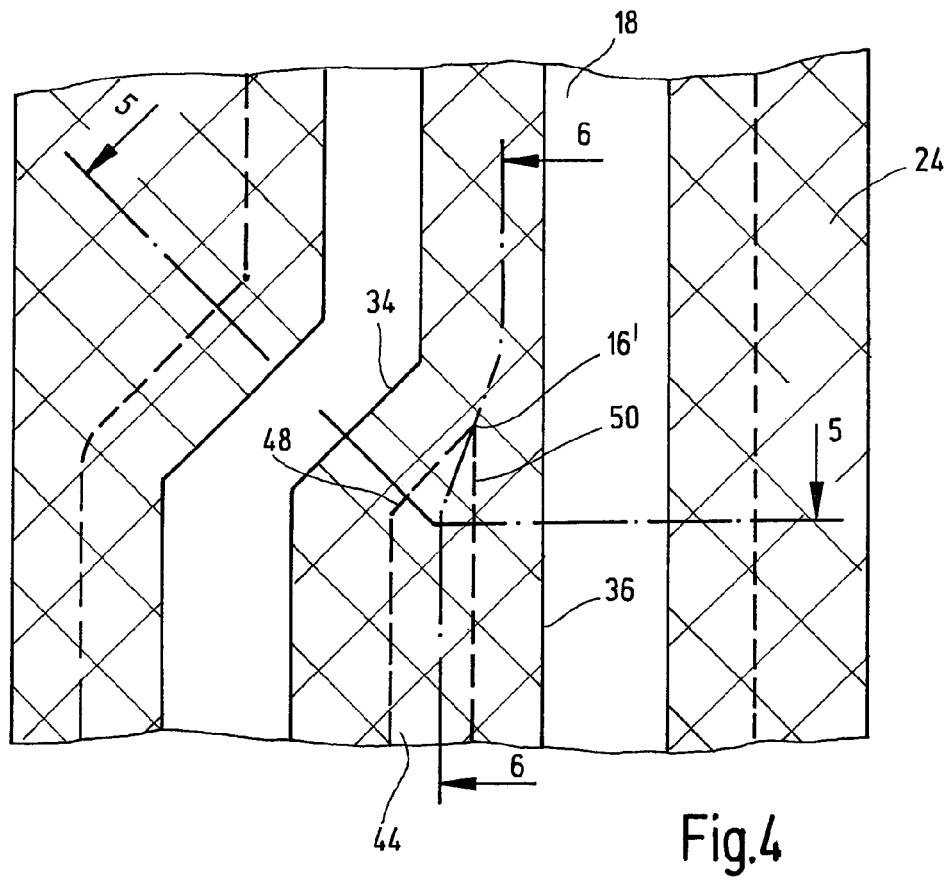
FIG. 4 is a fragmentary top view of an enlarged section of a first exemplary embodiment having an etching mask near the tip of a channel wall of a capillary channel.
Figure 5:
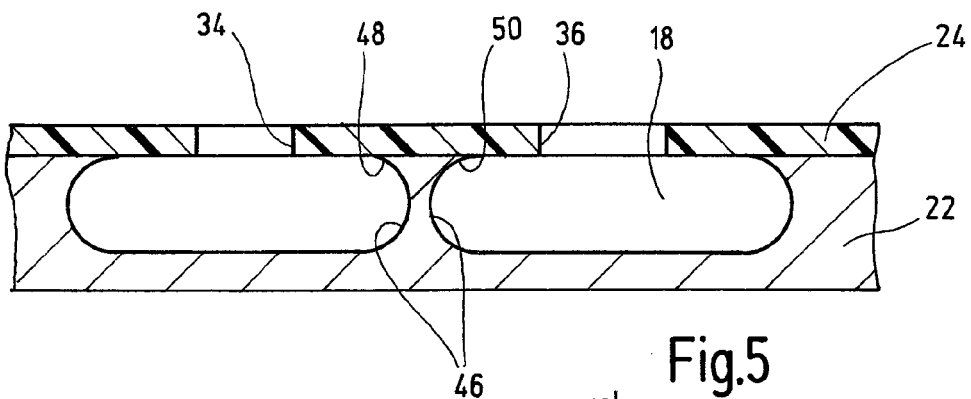
FIG. 5 is a cross-section taken along line 5-5 of FIG. 4 illustrating the lateral etching contour of a capillary channel.
Figure 6:
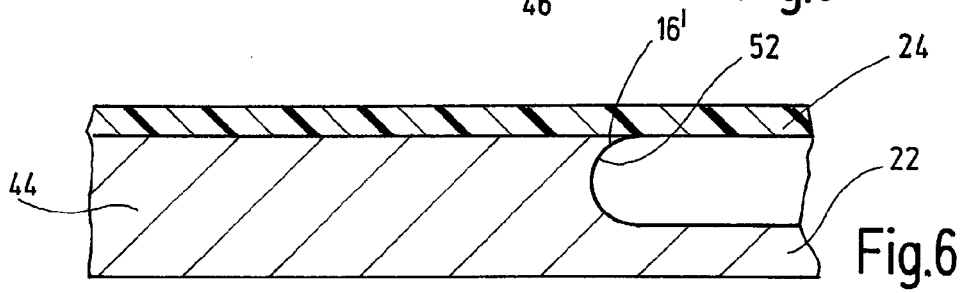
FIG. 6 is a cross-section taken along line 6-6 of FIG. 4 illustrating the lateral etching contour at the tip of a channel wall.

The basic geometric effects of the etching process in the area of the channel tips 16' are illustrated in FIGS. 4-6. FIGS. 5 and 6 only show the upper substrate area after a certain etching time where the lateral etching contours 46 only describe a circular line in the case of an isotropic etching action. Thus, lateral undercutting of the mask edges and side flanks 34, 36 result in undercut edges of the shaped member 48, 50 as shown in FIG. 5. Such undercuts are desirable in the area of the capillary channel 18 because they further improve the capillarity. However, as shown in FIG. 6, the undercut 52 results in a barb at both tips 16, 16' which can impair lancing the skin.

Figure 7:
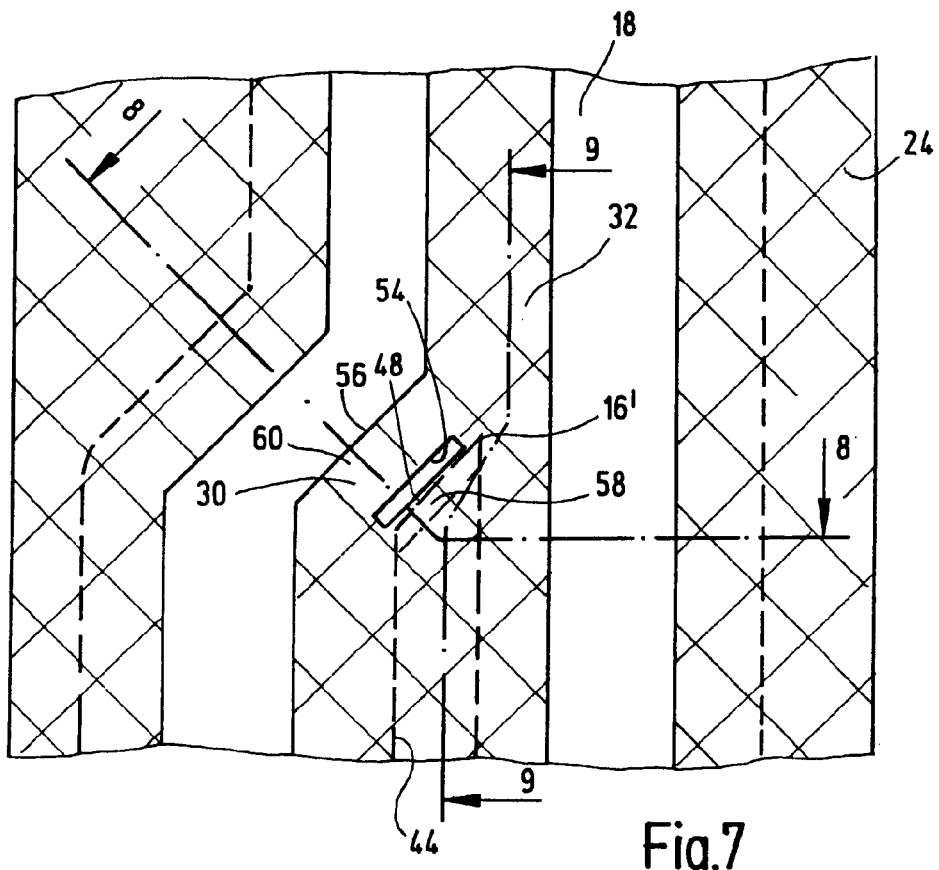
FIG. 7 is a fragmentary top view of an enlarged section of a second exemplary embodiment having an etching mask near the tip of a channel wall of a capillary channel and a compensation slot.
Figure 8:
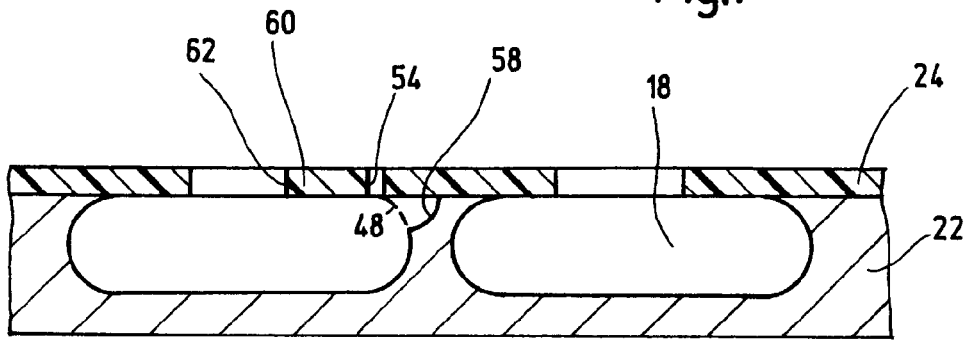
FIG. 8 is a cross-section taken along line 8-8 of FIG. 7 illustrating the lateral etching contours of a capillary channel including a compensation slot.
Figure 9:
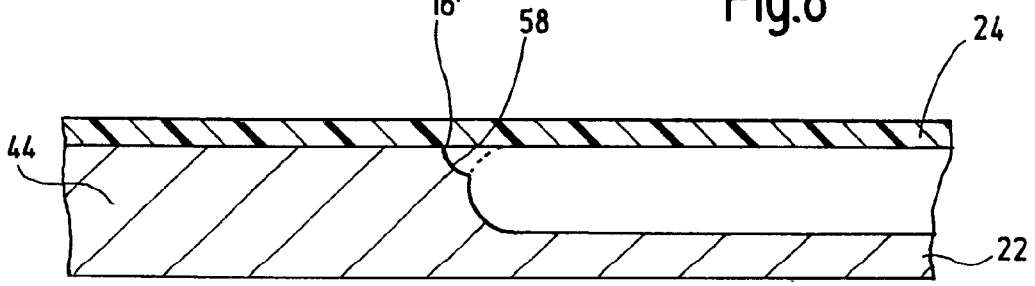
FIG. 9 is a cross-section taken along line 9-9 of FIG. 7 illustrating the lateral etching contour at the tip of a channel wall.

In order to address this impairment, a compensation slot 54 is designed in the mask 24 as shown in FIGS. 7 and 8. This slot extends at a lateral distance to an undercut edge 56 in the shaping area 30 of the mask 24 and ensures that the edges of the undercut 48 that would otherwise be formed are etched away. Hence, the etching agent which penetrates near the edge of the compensation slot 54 results in a rounding of the edge 58 while not producing a barb. The width of the mask strip 60 between the undercut edge 56 and the compensation slot 54 is advantageously less than the lateral undercut width. This should ensure that the compensation slot 54 has a substantially smaller inner width compared to the adjacent mask cut-out 62 so that the rounded edges 58 have a correspondingly smaller etching radius.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A process for producing a lancing element having a sharp tip for piercing a body part of a test subject, comprising:
   providing a mask having a shaping area to form the tip of the lancing element, a screening area which extends distally beyond the shaping area, and at least one side that is bent or concavely curved at the junction between the shaping area and the screening area;
   placing the mask on a flat material; and
   applying an etching agent to the mask and allowing the etching agent to act upon the flat material, wherein the screening area prevents the front of the tip from being etched off such that the etching produces a sharp tip by laterally undercutting side flanks of the shaping area and screening area.

2. The process of claim 1, further comprising providing the shaping area of the mask with a width that narrows in a direction toward the screening area.

3. The process of claim 1, further comprising providing the shaping area with at least one chamfered side.

4. The process of claim 1, further comprising providing the length of the screening area larger than a proximal undercutting width to offset the action of the etching agent.

5. The process of claim 1, further comprising providing a constriction in the mask that shapes the tip.

6. The process of claim 5, further comprising providing the width of the constriction as less than twice a lateral undercutting width.

7. The process of claim 5, further comprising providing the screening area with a width that widens in a distal direction away from the constriction.

8. The process of claim 1, further comprising providing the mask with a bridge section that widens in the distal direction relative to the tip to be formed.

9. The process of claim 1, further comprising etching the flat material such that an undercut is formed on an edge of the flat material.

10. The process of claim 1, further comprising applying the etching agent in a dipping bath or by spraying it onto the flat material.

11. The process of claim 10, further comprising applying the etching agent at an overpressure.

12. The process of claim 1, further comprising processing the flat material from roll to roll by photochemical mask etching.

13. The process of claim 1, further comprising selecting the thickness of the flat material from between 1 mm and 0.01 mm.

14. The process of claim 1, further comprising providing the mask with a channel slot and using the channel slot to form a semi-open capillary channel on the lancing element with walls whose distal ends are shaped as sharp tips.

15. The process of claim 14, further comprising providing the screening area as two screening areas for the tips of the two channel walls, each screening area being delimited on one side by the channel slot.

16. The process of claim 1, further comprising providing a second mask on a second side of the flat material and etching a pointed lancing shaft on one side of the flat material and a semi-open capillary channel with pointed channel walls on the other side of the flat material.

17. The process of claim 1, further comprising providing the mask with a compensation opening positioned laterally inward from an edge of the shaping area and etching away an edge contour of the flat shaped member from the edge through the compensation opening.

18. A process for producing a lancing element having a sharp tip for piercing a body part of a test subject, comprising:
   providing a mask having a shaping area to form the tip of the lancing element, a screening area which extends distally beyond the shaping area, and a compensation opening disposed at a lateral distance to an undercut edge the shaping area;

placing the mask on a flat material; and applying an etching agent to the mask and allowing the etching agent to act upon the flat material, wherein the screening area prevents the front of the tip from being etched off and the compensation opening prevents formation of a barb at or near the tip.

19. The process of claim 18, further comprising providing the compensation opening as a slot.

20. The process of claim 18, further comprising providing the compensation opening as a chain of holes.

21. The process of claim 18, further comprising providing the mask with an opening bordering the edge of the shaping area, wherein the compensation opening has a smaller width than the opening.

22. The process of claim 18, further comprising providing the mask with a bridge between the edge of the shaping area and the compensation opening.

23. The process of claim 18, further comprising positioning the compensation opening in at least one of the shaping area and the screening area.

24. The process of claim 18, further comprising providing the compensation opening laterally inward from a side edge of the mask that is bent or concavely curved.

* * * * *